(12) United States Patent
Rampalli et al.

(10) Patent No.: US 11,111,250 B2
(45) Date of Patent: Sep. 7, 2021

(54) POLYMORPHS OF RIBOCICLIB MONO SUCCINATE

(71) Applicant: SHILPA MEDICARE LIMITED, Raichur (IN)

(72) Inventors: Sriram Rampalli, Vizianagaram (IN); Lav Kumar Upalla, Vizianagaram (IN); Suryanarayan Cherukuvada, Vizianagaram (IN); Chanti Babu Patneedi, Vizianagaram (IN); Gopala Krishna Dasari, Vizianagaram (IN); Vijaya Murali Mohan Rao Seshagiri, Vizianagaram (IN)

(73) Assignee: SHILPA MEICARE LIMITED, Raichur (IN)

( * ) Notice: Subject to any disclaimer, the term of this patent is extended or adjusted under 35 U.S.C. 154(b) by 0 days.

(21) Appl. No.: 16/955,823

(22) PCT Filed: Dec. 20, 2018

(86) PCT No.: PCT/IB2018/060421
§ 371 (c)(1),
(2) Date: Jun. 19, 2020

(87) PCT Pub. No.: WO2019/123364
PCT Pub. Date: Jun. 27, 2019

(65) Prior Publication Data
US 2020/0339588 A1 Oct. 29, 2020

(30) Foreign Application Priority Data
Dec. 22, 2017 (IN) .............................. 201741046321
Dec. 22, 2017 (IN) .............................. 201741046322

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
None
See application file for complete search history.

(56) References Cited

U.S. PATENT DOCUMENTS

| 8,415,355 | B2 | 4/2013 | Brain et al. |
| 9,193,732 | B2 | 11/2015 | Calienni et al. |
| 2017/0342075 | A1 | 11/2017 | Chen et al. |

FOREIGN PATENT DOCUMENTS

| CN | 105085533 A | 11/2015 | |
| EP | 3156406 A1 | 4/2017 | |
| WO | 2016091221 A1 | 6/2016 | |
| WO | WO 2018/051280 A1 * | 3/2018 | ........... C07D 487/04 |

* cited by examiner

*Primary Examiner* — Brian J Davis (57) ABSTRACT

The present invention relates to novel crystalline and amorphous polymorphic forms of Ribociclib(1) mono succinate. (I) Said crystalline forms may be useful in the improved preparation of oral dosage forms for the treatment of cancer.

(I)

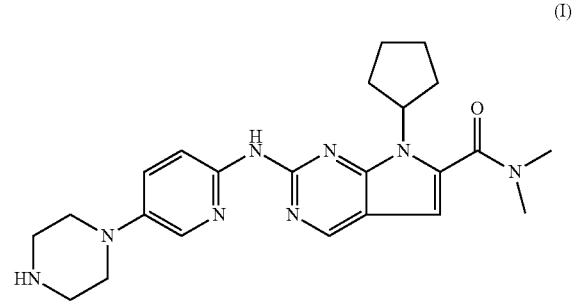

6 Claims, 9 Drawing Sheets

POLYMORPHS OF RIBOCICLIB MONO SUCCINATE

FIELD OF THE INVENTION

The present invention relates to novel stable crystalline and amorphous polymorphic forms of Ribociclib of formula (I) mono succinate and methods of preparing the same as well as pharmaceutically acceptable salts thereof.

The present invention mainly relates to novel stable crystalline polymorphic forms of Ribociclib mono succinate, said crystalline or amorphous forms may be commercially viable and lead to consistently produce as the stable material as per the processes according to the present invention.

BACKGROUND OF THE INVENTION

Ribociclib is chemically known as 7-Cyclopentyl-2-(5-piperazin-1-yl-pyridin-2-ylamino)-7H-pyrrolo [2,3-d]pyrimidine-6-carboxylic acid dimethylamide. 7-Cyclopentyl-2-(5-piperazin-1-yl-pyridin-2-ylamino)-7H-pyrrolo [2,3-d] pyrimidine-6-carboxylic acid dimethylamide or Ribociclib is an orally available cyclin-dependent kinase (CDK) inhibitor targeting cyclin D1/CDK4 and cyclin D3/CDK6 cell cycle pathway, with potential antineoplastic activity. Ribociclib specifically inhibits CDK4 and 6, thereby inhibiting retinoblastoma (Rb) protein phosphorylation. Inhibition of Rb phosphorylation prevents CDK-mediated G1-S phase transition, thereby arresting the cell cycle in the G1 phase, suppressing DNA synthesis and inhibiting cancer cell growth. Overexpression of CDK4/6, as seen in certain types of cancer, causes cell cycle deregulation.

Ribociclib mono succinate salt was approved by USFDA in Mar. 13, 2017 and is marketed under the brand name Kisqali® and is indicated for the treatment of for the treatment of postmenopausal women with hormone receptor (HR)-positive, human epidermal growth factor receptor 2 (HER2)-negative advanced or metastatic breast cancer.

Ribociclib mono succinate is a light yellow to yellowish brown crystalline powder. The molecular formula for Ribociclib mono succinate is $C_{23}H_{30}N_8O.C_4H_6O_4$ and the molecular weight is 552.64 g/mol (Free base: 434.55 g/mol).

As per EMEA scientific discussion the active substance is a slightly hygroscopic yellow to brown crystalline powder, soluble in acidic aqueous media, becoming less soluble as pH increases.

Polymorphism has been observed for Ribociclib mono succinate. Production of the correct polymorphic form is ensured by an XRPD method in the active substance specification. As described under the stability section, Ribociclib mono succinate form A has been demonstrated to be stable and not to convert into other polymorphic forms under long term and accelerated stability studies when stored in the proposed packaging.

Ribociclib is specifically anticipated in U.S. Pat. No. 8,415,355. The compound Ribociclib has valuable pharmacological properties and can be used, for example (1) as inhibitors of cyclin dependent kinases, in particular CDK1, CDK2, CDK3, CDK4, CDK5, CDK6 and CDK9; and (2) as modulators and/or inhibitors of glycogen synthesis kinase-3 (GSK-3). The process for the preparation of Ribociclib is delineated below.

This patent has not provided any insight about the impurity concern as well as solid state and purity of the final product of Ribociclib. The process appears cumbersome and involves the formation of large number of impurities.

John et al in U.S. Pat. No. 9,193,732 disclose a process for the preparation of Ribociclib and the succinate salt thereof. In addition this patent also describes the solid state characteristics of anhydrous Ribociclib mono succinate salt as well as monohydrate thereof.

The process for the preparation of Ribociclib mono succinate was schematically represented as below:

mono succinate salt of Form I and crystalline Form A of adipate, maleate and glycolate salts of Ribociclib. Further this patent application does not disclose any specific process for the preparation of Ribociclib.

Frank et al, in EP 3156406 discloses crystalline Ribociclib free base Form 1, Form 4, Form 6, Form 7 and Form 8. Further this patent application does not disclose any salt forms of Ribociclib and its preparation thereof.

The conversion of one polymorphic form into another polymorphic form can be unfavorable in pharmaceutical dosage forms such as tablets, often resulting in different However, when following the proposed route of synthesis the obtained ribociclib shows certain disadvantages with regard to its purity and or solid state.

Chen et al in US20170342075 disclosed different salt forms like crystalline form of hemi succinate salt of Form A, hygroscopicity, dissolution and pharmacokinetic properties. As a result thereof, the bioavailability of the active agent might be undesirably unpredictable. Consequently, active agents having different interchangeable polymorphs may lead to regulatory and commercial disadvantages since they very often do not fulfill the requirements of the corresponding regulation authorities such as the FDA and EMEA.

In view of the above it is pertinent to note that there exists an inherent need to develop stable crystalline form of Ribociclib and its salts having further improved physical and/or chemical properties besides high purity levels. Hence it was thought worthwhile by the inventors of the present application to explore novel process/crystallization process for the preparation of Ribociclib mono succinate, which may further improve the characteristics of drug Ribociclib and in developing the substantially pure stable crystalline forms of Ribociclib mono succinate consistently obtainable and amenable to scale-up.

As polymorphism has been given importance in the recent literatures owing to its relevance to the drugs having oral dosage forms due to its apparent relation to dose preparation/suitability in composition steps/bioavailability and other pharmaceutical profiles, stable polymorphic form of a drug has often remained the clear choice in composition due to various reason of handling, mixing and further processing including bioavailability and stability.

Exploring new polymorphic form for developing stable and pure forms of Ribociclib mono succinate which are amenable to scale up for pharmaceutically active useful compounds in the preparation of Ribociclib may thus provide an opportunity to improve the drug performance characteristics of products such as purity and solubility. Hence, inventors of the present application report a new polymorphic form, which is a stable and substantially pure form of Ribociclib mono succinate, which may be industrially amenable and usable for preparing the corresponding pharmaceutical compositions.

In view of above and overcome the prior art problems the present inventors had now developed a new polymorphic forms of Ribociclib and its salts. It was apparent to develop a process/or crystallization process resulting in the product, which is complying with the ICH requirements of quality parameters. Ribociclib mono succinate crystalline material was obtained by the process of the present invention is chemically stable and has been found with good dissolution properties.

Objective of the Invention

The main object of the invention relates to new stable polymorphic forms of Ribociclib mono succinate Yet another object of the present invention relates to crystalline forms of Ribociclib mono succinate, which is stable and substantially pure form, which may be industrially amenable and useful for preparing corresponding pharmaceutical compositions.

Yet another object of the present invention relates a process for the preparation of crystalline forms of Ribociclib mono succinate.

Yet another object of the present invention relates a process for the preparation of stable amorphous forms of Ribociclib mono succinate Yet another object of the present invention relates to a process for the preparation of crystalline and solvate forms of Ribociclib free base.

SUMMARY OF THE INVENTION

Aspects of the present invention relates to the new stable polymorphic forms of Ribociclib mono succinate.

In one aspect of present invention relates to crystalline Ribociclib mono succinate Form-SRS-I characterized by X-ray powder diffraction pattern comprising peaks at 9.0, 13.0, 15.2, 16.5, 17.3, 18.3, 20.0, 21.4, 21.6, 22.1, 23.6, 23.9 and 28.0±0.2 2θ°

Crystalline Ribociclib mono succinate Form-SRS-I, is further characterized by DSC isotherm comprising endothermic peaks ranging between 175 to 185° C.

Further aspect of present invention relates to process for the preparation of crystalline Ribociclib mono succinate Form-SRS-I comprising:
 a) dissolving succinic acid in solvent;
 b) adding Ribociclib;
 c) concentrating the reaction mass;
 d) optionally adding second solvent followed by distillation; and
 e) Isolate the crystalline Ribociclib mono succinate.

Another aspect of the present invention relates to crystalline Ribociclib mono succinate Form-SRS-II characterized by X-ray powder diffraction pattern comprising peaks at from 8.8, 12.9, 13.9, 14.4, 15.2, 16.2, 19.0, 19.8, 21.2, 21.9 and 27.7±0.2 2θ°

Crystalline Ribociclib mono succinate Form-SRS-II, is further characterized by DSC isotherm comprising endothermic peaks ranging between 198 to 208° C.

Further aspect of present invention relates to process for the preparation of crystalline Ribociclib mono succinate Form-SRS-II comprising:
 a) providing a reaction mixture of Ribociclib succinate in ethyl acetate;
 b) slurried the reaction mass;
 c) filter the reaction mass; and
 d) vacuum dried to obtain the crystalline Ribociclib mono succinate Form—SRS-II.

Yet another object of the present invention relates a process for the preparation of stable amorphous forms of Ribociclib mono succinate Yet another object of the present invention relates to crystalline and solvate forms of Ribociclib free base, which is stable and substantially pure form, which may be industrially amenable and useful for preparing corresponding pharmaceutical compositions.

Yet another object of the present invention relates to a process for the preparation of crystalline and solvate forms of Ribociclib free base.

DETAILED DESCRIPTION OF THE INVENTION

Although several polymorphs of Ribociclib mono succinate have been identified and well known in the literature, each polymorphic form can be distinguished using several different analytical parameters, alone or in combination, such as, but not limited to, powder X-ray diffraction pattern peaks or combinations of two or more peaks. However, the present inventors now developed a new stable crystalline polymorphic form, which are different from the prior-art polymorphic forms disclosed in the literature.

In one embodiment of the present invention relates to crystalline Ribociclib mono succinate Form-SRS-I characterized by X-ray powder diffraction pattern comprising peaks at 9.0, 13.0, 15.2, 16.5, 17.3, 18.3, 20.0, 21.4, 21.6, 22.1, 23.6, 23.9 and 28.0±0.2 2θ°;

Crystalline Ribociclib mono succinate Form-SRS-I is further characterized by X-ray powder diffraction pattern comprising at 2θ° peaks selected from 4.8, 10.7, 13.5, 14.2, 16.2, 18.0, 19.2, 20.9, 22.7, 23.1, 24.4, 25.4, 26.2, 26.7 and 28.4±0.2 2θ°.

Crystalline Ribociclib mono succinate Form-SRS-I, is further characterized by DSC isotherm comprising endothermic peaks ranging between 175 to 185° C.

In another embodiment the present invention further relates to liquid state $^1$H-NMR spectrum comprising chemical shift at 26.1±0.2, 114.7±0.2, 154.8±0.2 and 167.8±0.2, ppm The present invention further provides a process for the preparation of Crystalline Ribociclib mono succinate Form-SRS-I characterized by X-ray powder diffraction pattern comprising characteristic 2θ° peaks at 9.0, 13.0, 15.2, 16.5, 17.3, 18.3, 20.0, 21.4, 21.6, 22.1, 23.6, 23.9 and 28.0±0.2 2θ°, wherein process for the preparation of Crystalline Ribociclib mono succinate Form-SRS-I comprising the steps of:
a) dissolving succinic acid in first solvent;
b) adding Ribociclib;
c) concentrating the reaction mass;
d) optionally adding second solvent followed by distillation; and
e) isolate the crystalline Ribociclib mono succinate.

Solvent used in step (a) is selected from alcohol (C1-5) or Ketones (C3-6) or organic solvents (C1-8 alkanes, dimethyl formamide, dimethyl acetamide, N-methyl pyrrolidine) or halogenated organic solvents (Methylene dichloride, Ethylene dichloride) or Ethers (Methyl tertiary butyl ether, tetrahydrofuran) or sulphoxides (dimethyl sulphoxide) or esters (Ethyl acetate, benzyl acetate, isoamyl acetate) or water or mixtures thereof.

Solvent used in step (d) is selected from selected from solvent selected from alcohol (C1-5) or Ketones (C3-6) or organic solvents (C1-8 alkanes, dimethyl formamide) or halogenated organic solvents (Methylene dichloride, Ethylene dichloride) or Ethers (Methyl tertiary butyl ether, tetrahydrofuran) or sulphoxides (dimethyl sulphoxide) or esters (Ethyl acetate, benzyl acetate, isoamyl acetate) or water or mixtures thereof.

Crystalline Ribociclib mono succinate Form-SRS-I obtained by the above process is hydrate and having a moisture content of less than 5.0%. The Crystalline Ribociclib mono succinate Form-SRS-I obtained by this process is stable and free of process related impurities.

The present inventors analyzed Crystalline Ribociclib mono succinate Form-SRS-I for Hygroscopic study. However, the present inventors found that the Crystalline Ribociclib mono succinate Form-SRS-I obtained by the present invention is stable at all temperature ranging between 0-80° C.

Further, the study of Crystalline Ribociclib mono succinate Form-SRS-I at 90% relative humidity in desiccator at 25° C. containing saturated potassium chloride solution are kept in glass petri-dish and placed it into desiccator, the samples were withdrawn and analyzed after three hours shows raise in water content from 2 to 5%, which yields Ribociclib mono succinate having overall in 7 to 10% of water content. However, due to anticipated gain of water content in at 90% relative humidity said form may be utilized with caution and further studies of stabilities in preparing any solid oral dosage form.

The above results indicates that the Crystalline Ribociclib mono succinate Form-SRS-I was observed to absorb moisture at about 90% relative humidity. The sample obtained after 3 hours was dried at 60-80° C. and further sent for PXRD analysis. The PXRD obtained was found to resembles with the Crystalline Ribociclib mono succinate Form-SRS-I. This data shows that the Crystalline Ribociclib mono succinate Form-SRS-I is a stable form of Crystalline Ribociclib mono succinate and may be utilized in the preparation of pharmaceutical composition. On normal atmospheric conditions, there was no moisture absorption observed in Form-SRS-I.

It was also observed by inventors of the present application that Form-SRS-II also becomes stable as anhydrous form. This form may also be produced consistently at industrial scale quantities.

Crystalline Ribociclib mono succinate Form-SRS-II characterized by X-ray powder diffraction pattern comprising peaks at from 8.8, 12.9, 13.9, 14.4, 15.2, 16.2, 19.0, 19.8, 21.2, 21.9 and 27.7±0.2° 2θ

Crystalline Ribociclib mono succinate Form-SRS-II is further characterized by X-ray powder diffraction pattern comprising at 2θ° peaks selected from 5.0, 7.5, 9.8, 10.6, 17.9, 20.9, 21.5, 24.6, 25.5, 26.2, 26.9 and 28.7±0.2° 2θ.

Crystalline Ribociclib mono succinate Form-SRS-II is further characterized by DSC isotherm comprising endothermic peaks ranging between 198 to 208° C.

The present invention further provides a process for the preparation of Crystalline Ribociclib mono succinate Form-SRS-II comprising the steps of:
a) providing a reaction mixture of Ribociclib succinic acid in ethyl acetate;
b) slurried the reaction mass;
c) filter the reaction mass; and
d) vacuum dried to obtain the crystalline Ribociclib mono succinate Form—SRS-II.

Further embodiment of the present invention provides Crystalline Ribociclib mono succinate Form-SRS-II obtained by the present invention is free of other polymorphic impurities, wherein said crystalline form is present in a solid form greater than 99.9% by weight.

Crystalline Ribociclib mono succinate Form-SRS-II is found to be a very stable crystal lattice which is adequately stable to handle and store for longer time without any significant or measurable change in its morphology and physicochemical characteristics. Crystalline Ribociclib mono succinate Form-SRS-II retains its nature even on exposure to uncontrolled environmental conditions. This stable form thus, offers various advantages in terms of storage, shelf life and favorable impurity profile.

Any form of Crude or Pure Ribociclib mono succinate obtained by any process may be used for preparing any of the Crystalline or amorphous Ribociclib mono succinate forms disclosed in the present invention. Ribociclib mono succinate forms disclosed in the present invention may have one or more advantageous and desirable properties compared to the known Crystalline Ribociclib mono succinate forms, which are not limited to better stability, hygroscopicity, high solubility and high purity leading to improved storage and distribution.

The process related impurities, including degradation products and other medium dependent impurities like residual solvent, that appear in the impurity profile of the Ribociclib mono succinate can be substantially removed by the process of the present invention resulting in the formation pure Ribociclib mono succinate. A substantially pure product i.e. crystalline Ribociclib mono succinate having purity more than 99.9% (by HPLC) can be obtained in high yield by the process of the present invention.

The Ribociclib mono succinate described herein may be characterized by X-ray powder diffraction pattern (XRPD) and IR absorption spectra and Thermal techniques such as differential scanning calorimetric (DSC) Analysis and TGA and solid state NMR. The samples of Ribociclib mono succinate were analyzed by XRPD on a Bruker AXS D8 Advance Diffractometer using X-ray source—Cu Kα radiation using the wavelength 1.5418 Å. DSC was done on a Perkin Elmer instrument. Illustrative example of analytical data for the Ribociclib mono succinate obtained in the Examples is set forth in the FIGS. 1-7.

The Ribociclib or its mono succinate salt used in the present invention is prepared by any of the conventional processes disclosed in the prior art.

The crude Ribociclib or its mono succinate salt obtained from the above stage may be purified by treating the compound of the formula (I) or a reaction mixture or a solvated form thereof is treated with an acid selected from methane sulphonic acid, sulphuric acid, trifluoro-methanesulphonic acid, difluoromethanesulphonic acid, dichloroacetic acid, glucornic acid, gluconic acid, glycols and glycol ethers; to form a salt of the compound of the formula (I) which precipitates from the solution containing the solvated compound of the formula (I), the salt of the compound of the formula (I) is then treated with an aqueous basic solution to precipitate the pure form of compound of the formula (I), preferably at a temperature of from 15° C. to 45° C., most preferably from 25° C. to 35° C. If required, repeat again the acidification followed by basitication to obtained desired purity, which is greater than 99.5%.

The Ribociclib or its mono succinate salt is dissolved in a solvent selected from solvent selected from alcohol (C1-3) or Ketones (C3-6) or organic solvents (C1-8 alkanes, dimethyl formamide) or halogenated organic solvents (Methylene dichloride, Ethylene dichloride) or Ethers (Methyl tertiary butyl ether, tetrahydrofuran) or sulphoxides (dimethyl sulphoxide) or esters (Ethyl acetate, benzyl acetate, isoamyl acetate) or water or mixtures thereof. To the obtained solution acid was added at a temperature ranging from −10 to 30° C. for 30 min to 2 hrs to yield wet product, which was dried under vacuum at 50-55° C. for 2 hrs to yield Ribociclib or its acid salt.

The obtained Ribociclib acid salt is dissolved in a solvent selected from solvent selected from alcohol (C1-4) or Ketones (C3-6) or organic solvents (C1-8 alkanes, dimethyl formamide, toluene, xylene) or halogenated organic solvents (Methylene dichloride, Ethylene dichloride) or Ethers (Methyl tertiary butyl ether, tetrahydrofuran, Di-isopropyl ether) or sulphoxides (dimethyl sulphoxide) or esters (Ethyl acetate, benzyl acetate, isoamyl acetate) or water or mixtures thereof at a temperature ranging from 25–30° C. and stirred for 30 min to get clear solution. The obtained solution was treated with an alkaline solution, wherein alkaline solution used is prepared using a base selected from organic base such as triethylamine, methylamine, pyridine, imidazole, benzimidazole; or inorganic base selected from carbonates such as sodium carbonate, potassium carbonate, calcium carbonate, ammonium carbonate; hydroxides such as sodium hydroxide, potassium hydroxide, calcium hydroxide, ammonium hydroxide, barium hydroxide, magnesium hydroxide, lithium hydroxide, zinc hydroxide; bicarbonates such as sodium bicarbonate, potassium bicarbonate, ammonium bicarbonate, calcium bicarbonate, magnesium bicarbonate; in a solvent selected from organic solvent or water. The reaction mass was stirred for 30 min to 4 hrs depending on the acid used. After completion of the reaction, the reaction mass was cooled to a temperature ranging from 0–10° C. and maintained the reaction mass under stirring for 30 min to 4 hrs. The precipitated product was filtered, washed with organic solvent or a mixture of organic solvent or mixture of organic solvent and water to get wet cake, which was dried under vacuum at 50-85° C. for 3 hrs to 6 hrs to yield pure Ribociclib.

Figure 1:
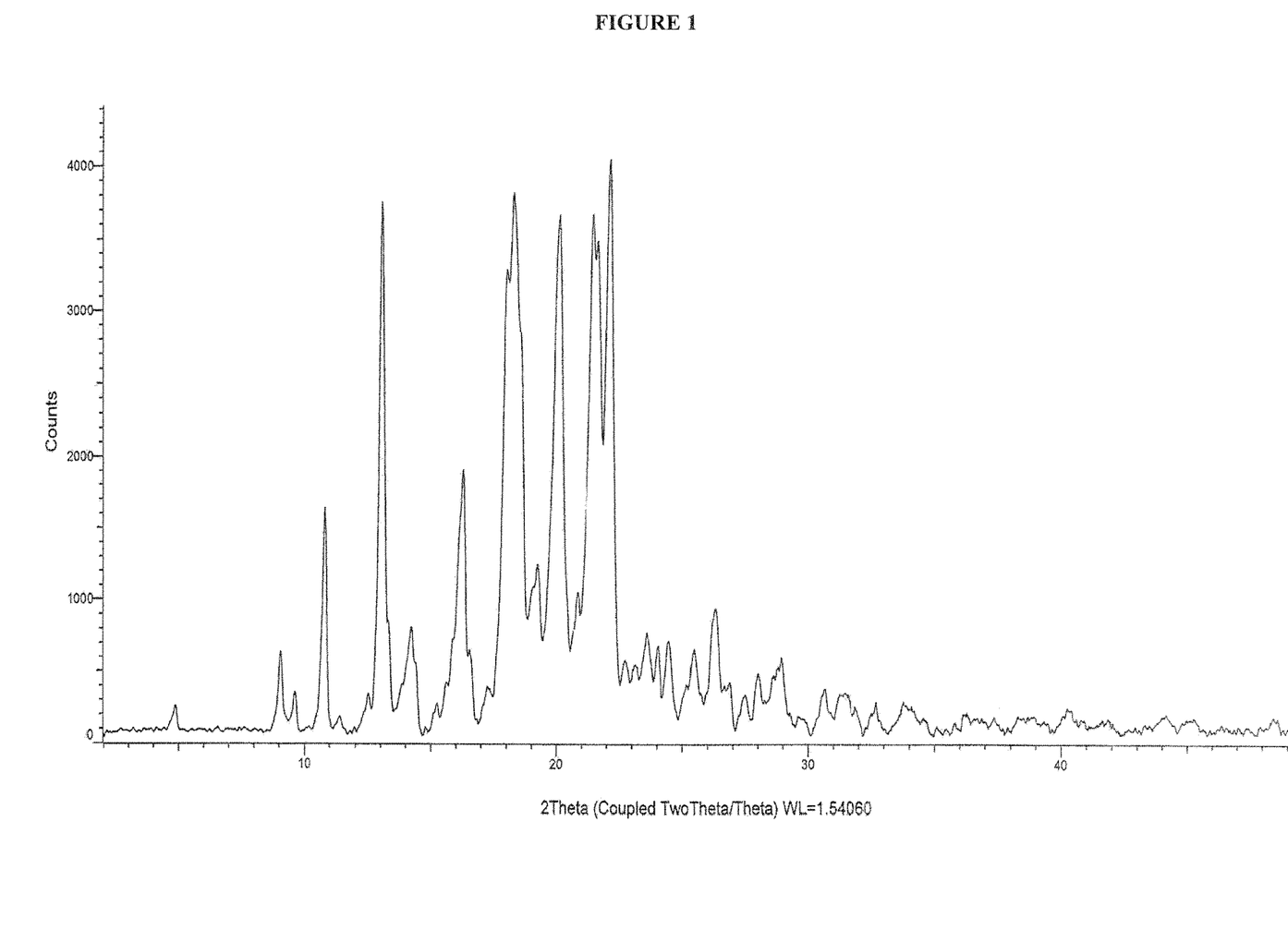
FIG. 1 is an example of X-ray powder diffraction ("XRPD") pattern of crystalline Ribociclib mono succinate Form-SRS-I obtained according the present invention.
Figure 2:
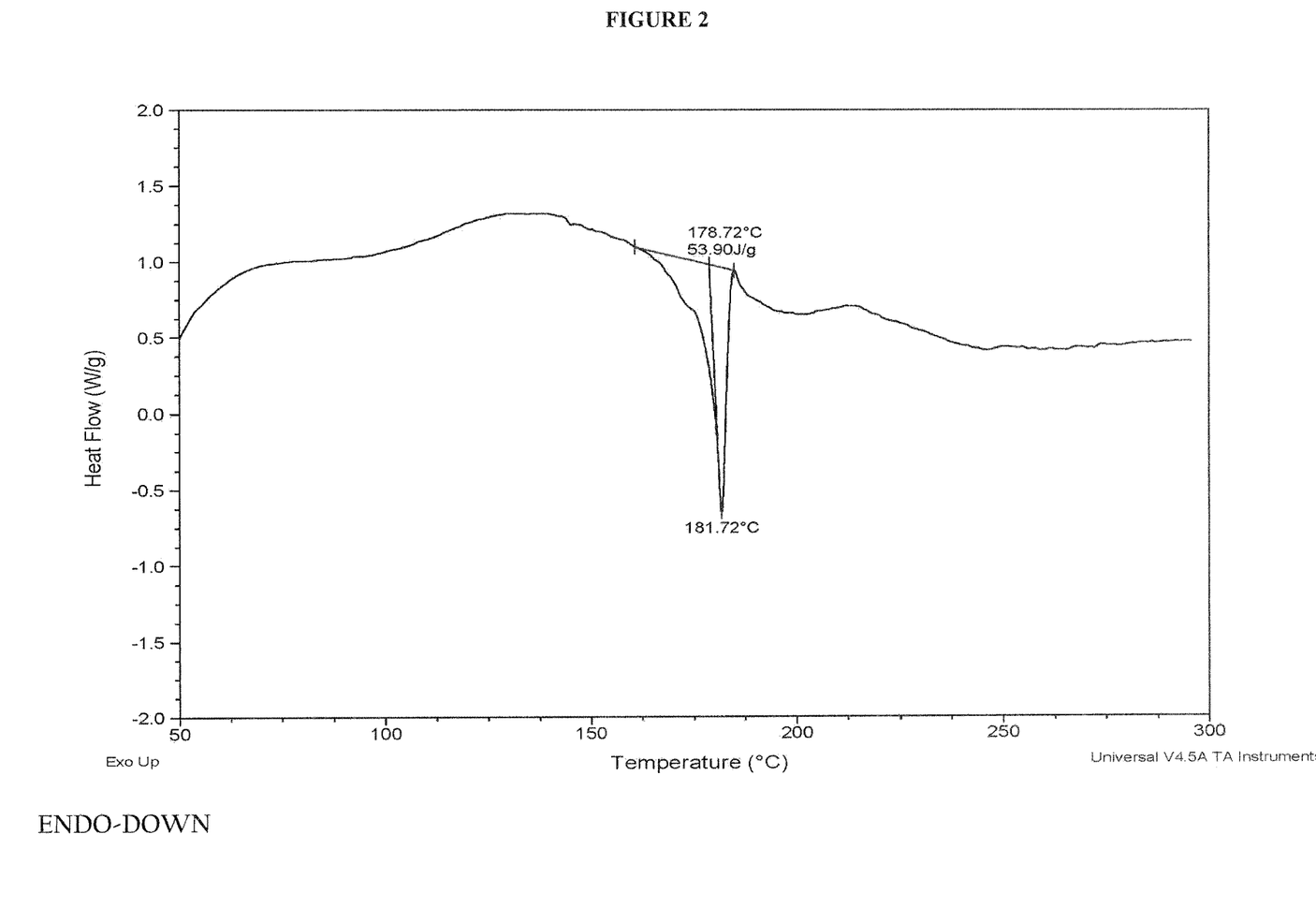
FIG. 2 is an example of DSC endotherm of crystalline Ribociclib mono succinate Form-SRS-I obtained according the present invention.
Figure 3:
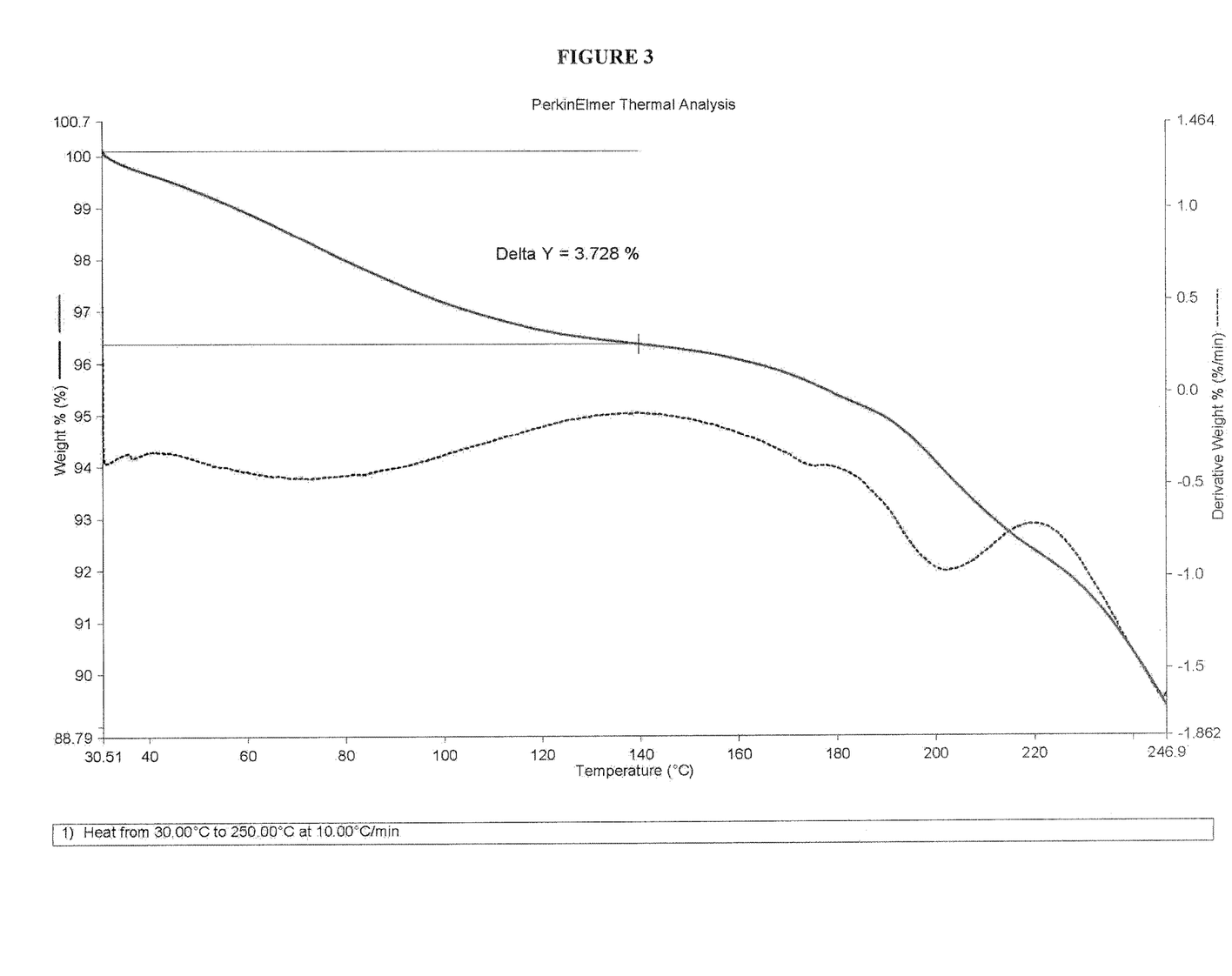
FIG. 3 is an example of TGA thermogram of crystalline Ribociclib mono succinate Form-SRS-I obtained according the present invention.
Figure 4:
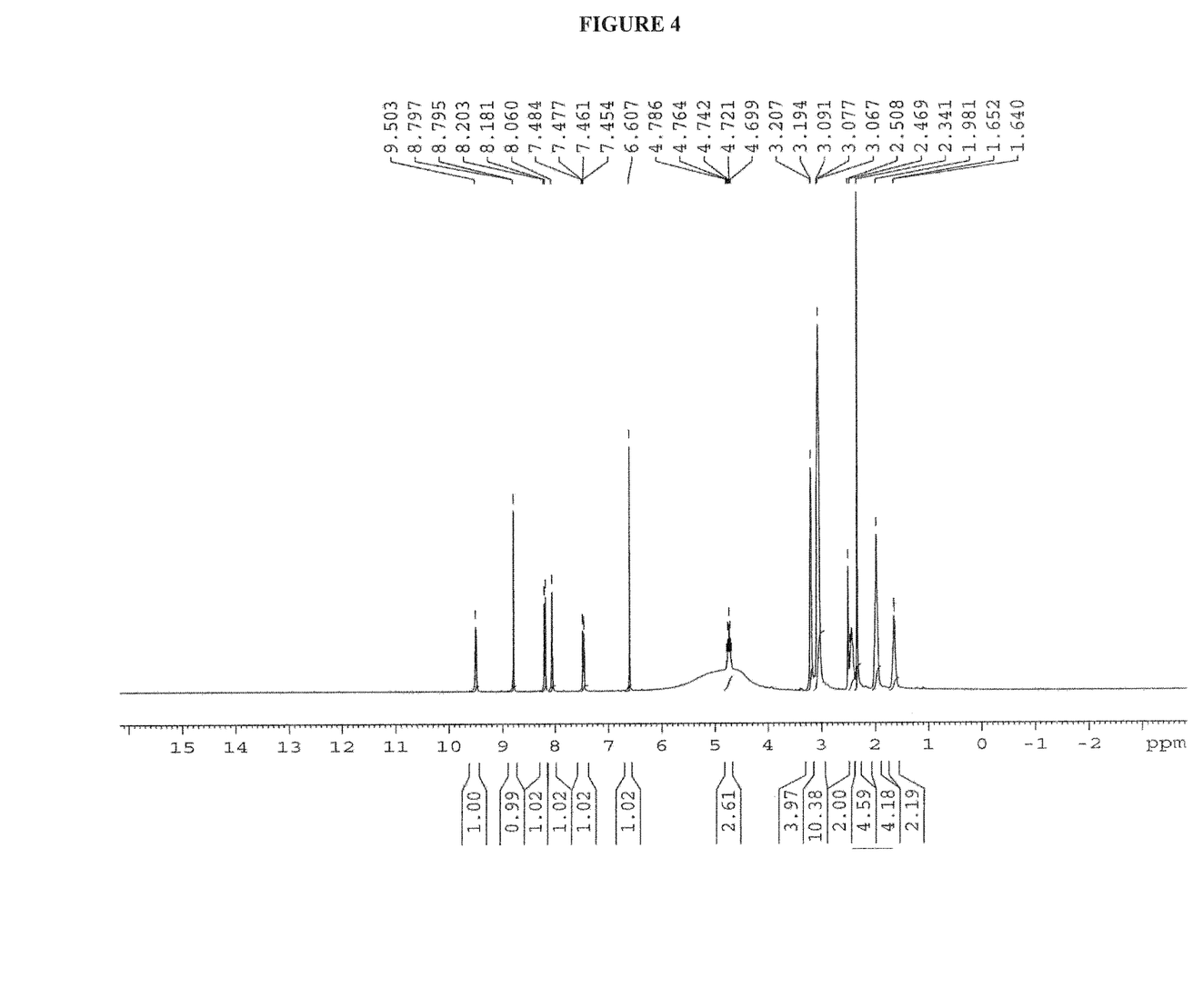
FIG. 4 is an example of ¹H NMR spectrum of crystalline Ribociclib mono succinate Form-SRS-I obtained according the present invention.
Figure 5:
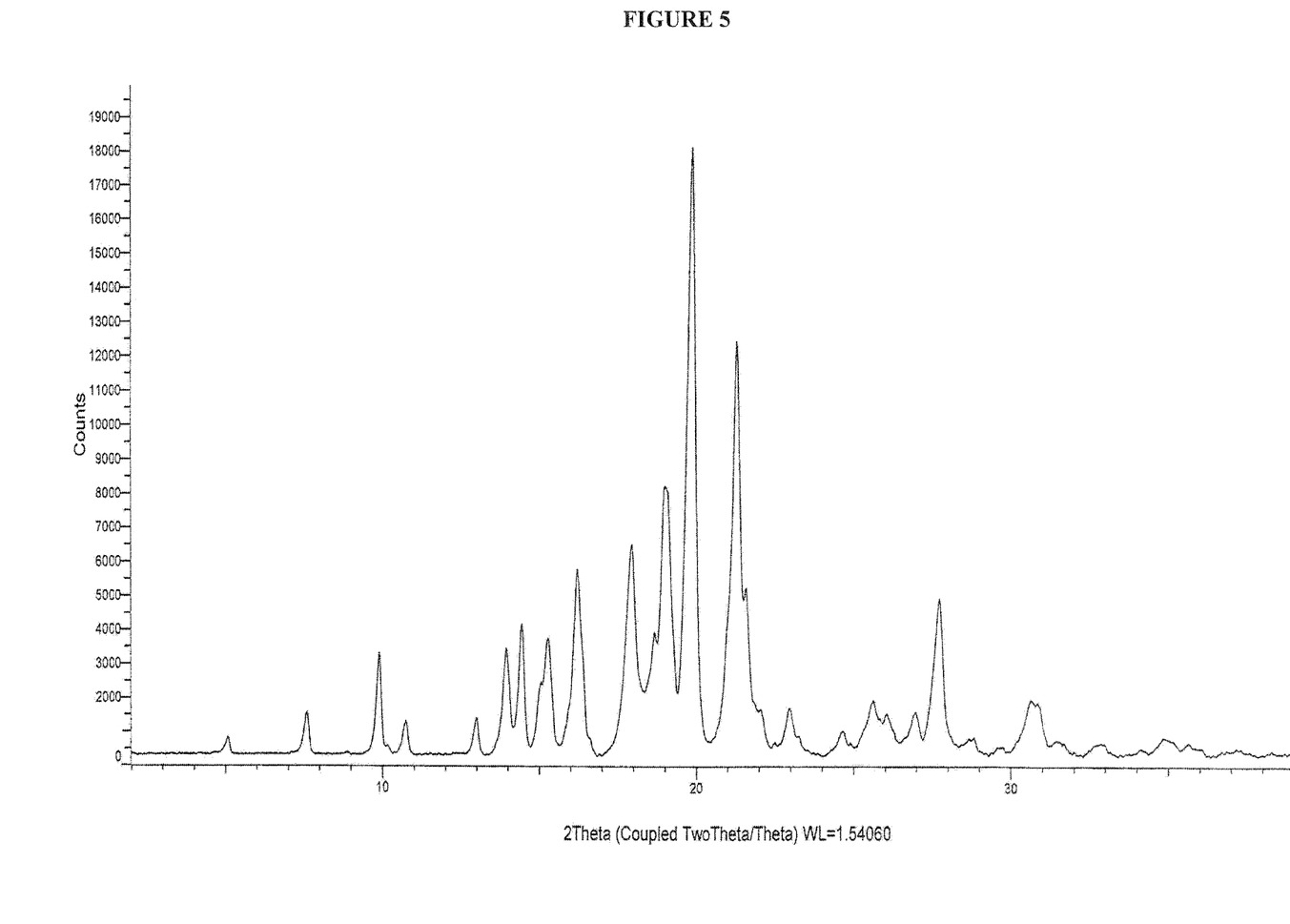
FIG. 5 is an example of X-ray powder diffraction ("XRPD") pattern of Ribociclib mono succinate Form-SRS-II obtained according the present invention.
Figure 6:
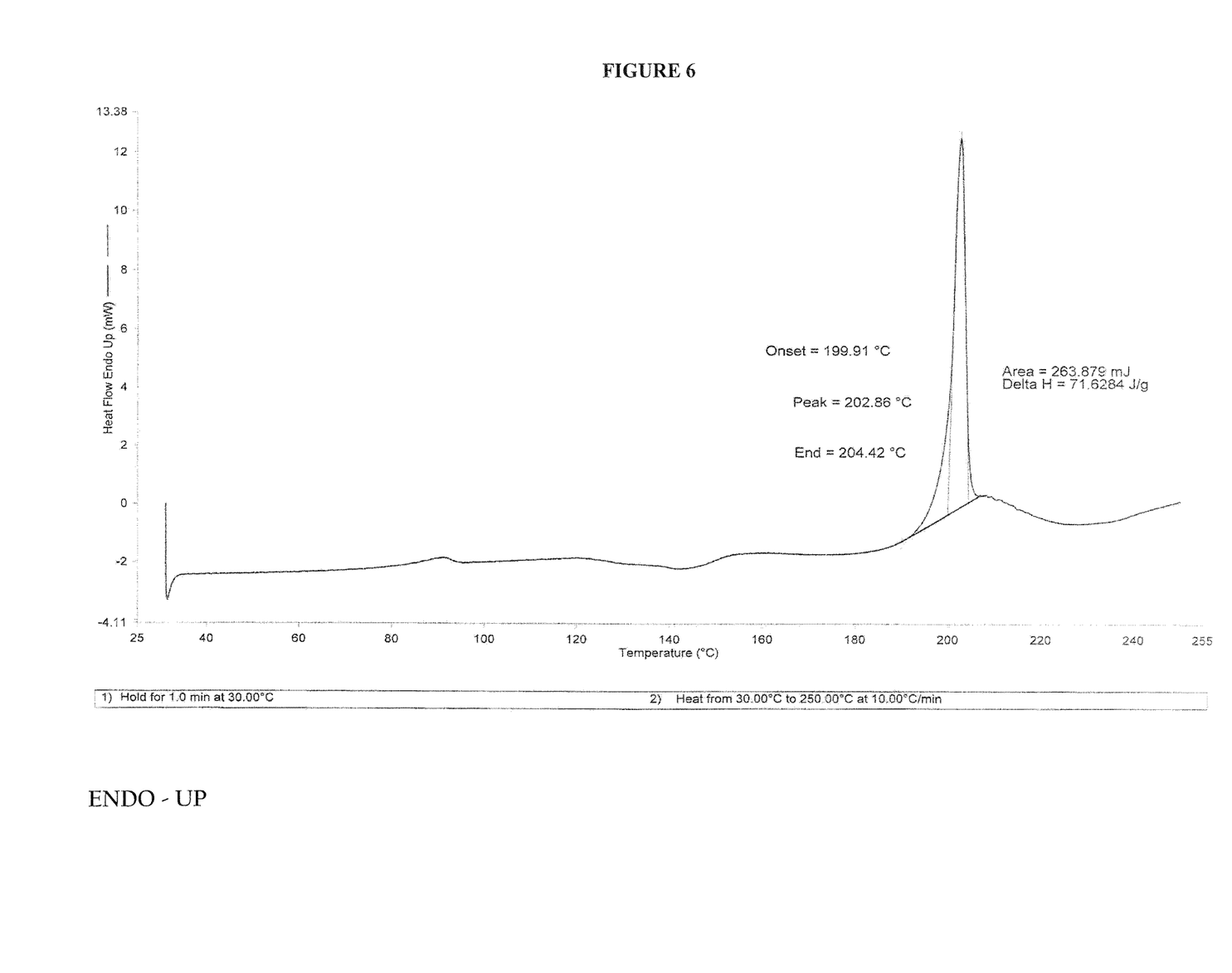
FIG. 6 is an example of DSC endotherm of Ribociclib mono succinate Form-SRS-II obtained according the present invention.
Figure 7:
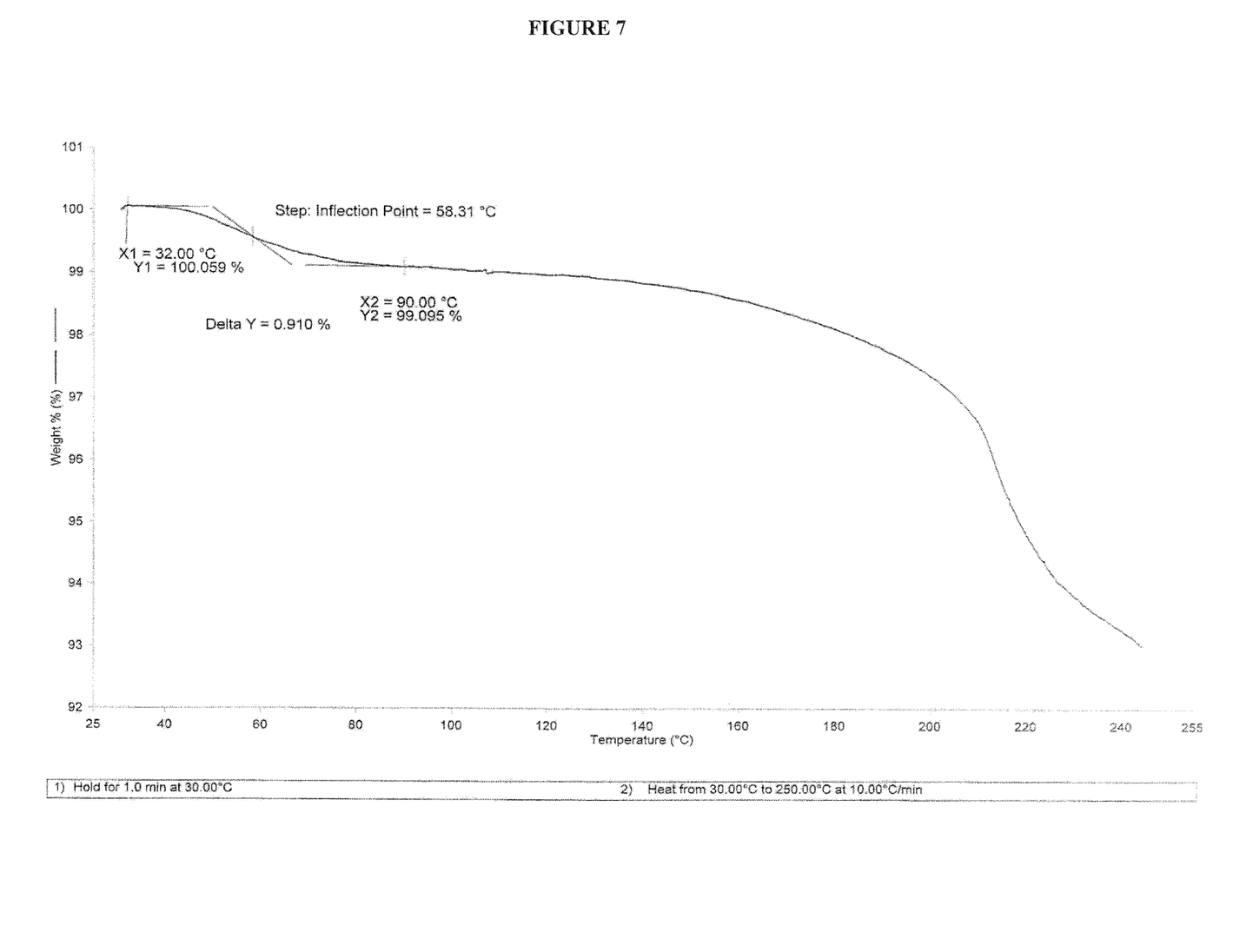
FIG. 7 is an example of TGA thermogram of Ribociclib mono succinate Form-SRS-II obtained according the present invention.
Figure 8:
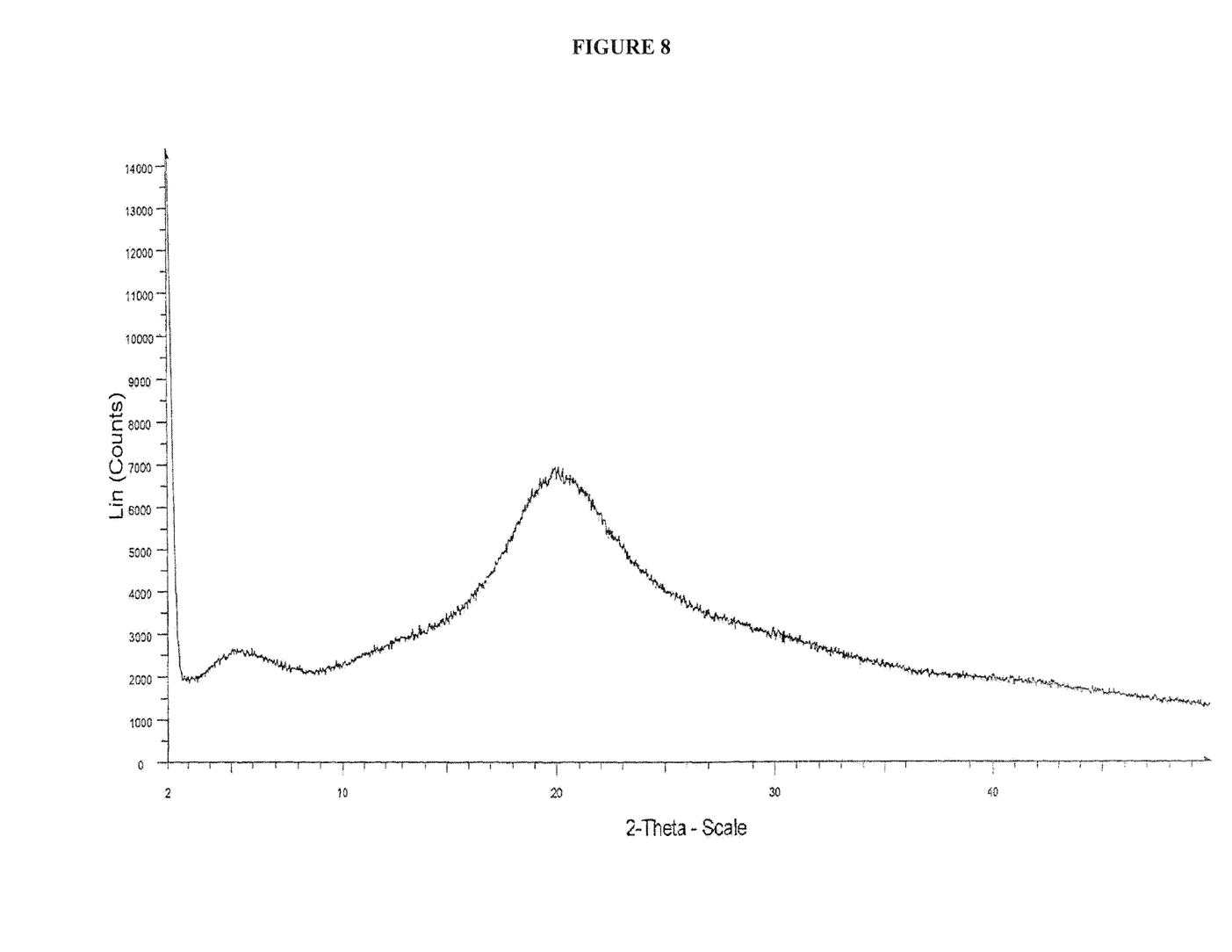
FIG. 8 is an example of X-ray powder diffraction ("XRPD") pattern of amorphous Ribociclib mono succinate obtained according the present invention.

In one embodiment of the present invention relates to new stable amorphous forms of Ribociclib mono succinate Yet another embodiment of the present invention relates a process for the preparation of stable amorphous forms of Ribociclib mono succinate In another embodiment of the present invention relates to amorphous Ribociclib mono succinate characterized by X-ray powder diffraction pattern as disclosed in FIG. 8.

Amorphous Ribociclib mono succinate, wherein process for the preparation of Amorphous Ribociclib mono succinate comprising the steps of:

a) dissolving Ribociclib mono succinate in a solvent; and
b) isolating amorphous Ribociclib mono succinate wherein solvent selected from alcohol used is selected from methanol, ethanol, isopropanol, 2-propanol, 1-butanol, t-butyl alcohol, 1-pentanol, 2,2,2-trifluoroethanol and 2-pentanol, water or mixture thereof; isolating amorphous form of Ribociclib mono succinate is by solvent evaporation technique such as distillation using a rotational evaporator, freeze drying (lyophilization), spray drying and agitated thin film drying (ATFD) are used.

The Amorphous Ribociclib mono succinate obtained by this process is stable and free of process related impurities.

In another embodiment, the present invention provides Amorphous Ribociclib mono succinate obtained by the present invention is free of other polymorphic impurities, wherein said crystalline form is present in a solid form greater than 99.9% by weight.

Figure 9:
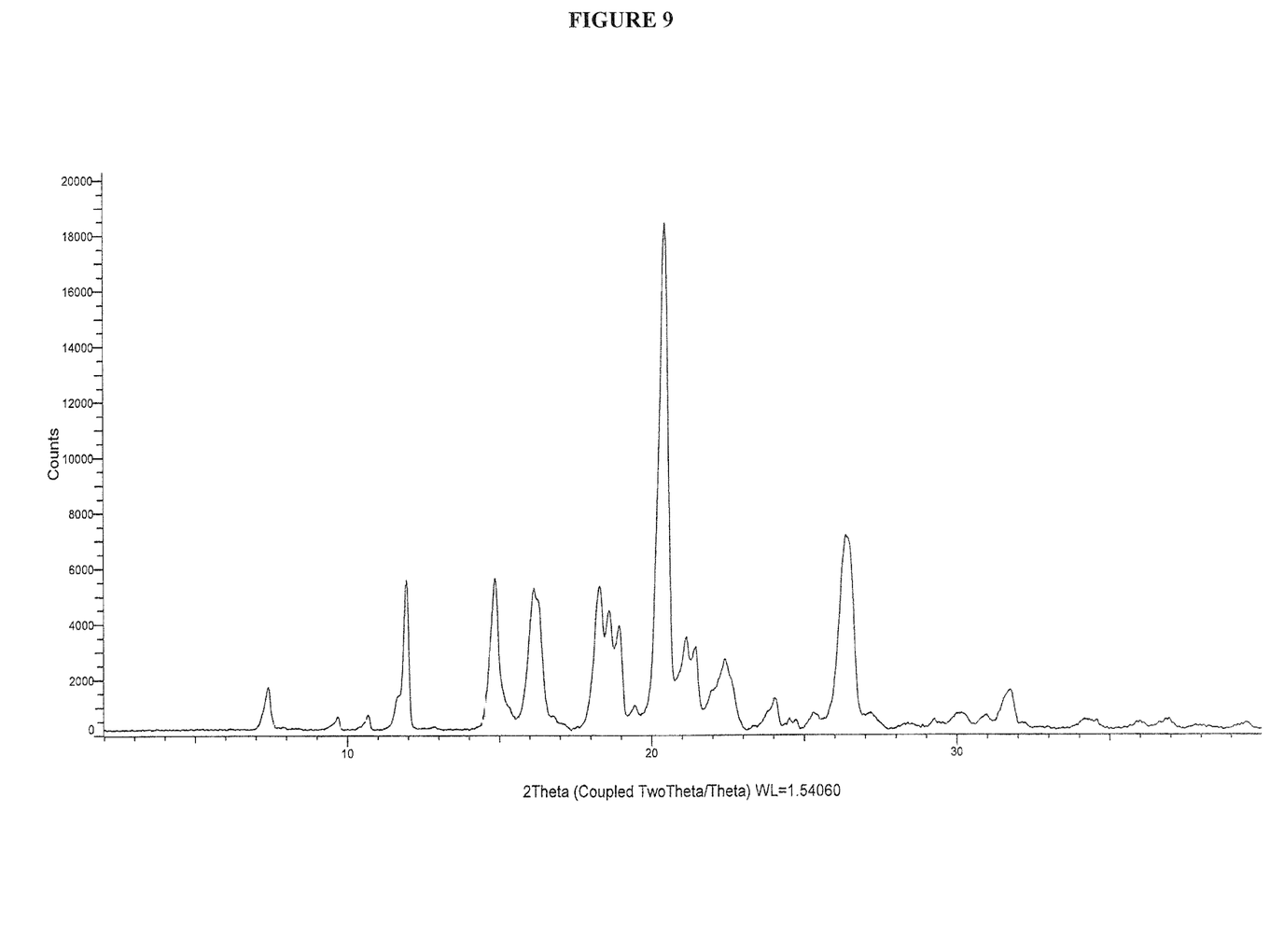
FIG. 9 is an example of X-ray powder diffraction ("XRPD") pattern of crystalline Ribociclib base obtained according the present invention.

In another embodiment of the present invention relates to crystalline Ribociclib free base. In another embodiment the present invention further relates to process for the preparation of crystalline Ribociclib base comprises dissolving in a solvent selected from alcohol (C1-5) at 25-30° C. Reaction mass was stirred for 5 to 30 minutes and filtered directly into a buchi rotavapor flask. Rotavaporization was performed at 40-60° C. with step-wise decrease of pressure from 916 mbar to 50 mbar for 120 minutes to yield crystalline Ribociclib base having PXRD pattern as disclosed in FIG. 9.

In another embodiment of the present invention relates to solvates of Ribociclib, wherein solvate is selected from 2-Methoxy ethanol solvate and DMSO solvate.

In another embodiment of the present invention further relates to process for the preparation of solvates of Ribociclib, wherein solvate is selected from 2-Methoxy ethanol solvate and DMSO solvate comprises reacting ribociclib base with specified solvent at 25-30° C. The obtained reaction mass was stirred for 30 minutes to 1 hour 30 minutes at 40-70° C. The obtained reaction mass was cooled to 25-30° C. and again stirred the reaction mass for 30 minutes to 1 hour 30 minutes at 25-30° C. Filtered and washed with specified solvent to yield corresponding solvate. Dried the material at 55-60° C. under vacuum for 12-15 hours.

The obtained pure Ribociclib was analyzed, if it is not matching with the desired purity; again repeat the process by treating the Ribociclib with acid to prepare the corresponding salt, followed by treating with an alkali solution to obtain substantially pure Ribociclib having a purity of greater than 99.5% and meeting the ICH guidelines.

The process related impurities that appear in the impurity profile of the Ribociclib (I) may be substantially removed by the process of the present invention resulting in the formation of substantially Ribociclib (I), which meets the ICH guidelines.

The merit of the process according to the present invention resides in that product isolated after drying is stable and having a purity of greater than 99.5% purity by HPLC, which was not disclosed in any of the prior-art. The product obtained as per the present invention is highly pure than the any of the prior-art products obtained. Till now no publication discloses a purity of greater than 99.5%.

Solubility is one of the important parameters to achieve desired concentration of drug in systemic circulation for achieving required pharmacological response. Poorly water soluble drugs often require high doses in order to reach therapeutic plasma concentrations after oral administration. Low aqueous solubility is the major problem encountered with formulation development of new chemical entities as well as generic formulation development. Most of the drugs are either weakly acidic or weakly basic having poor aqueous solubility. The improvement of drug solubility thereby its oral bio-availability remains one of the most challenging aspects of drug development process especially for oral-drug delivery system. The poor solubility and low dissolution rate of poorly water soluble drugs in the aqueous gastrointestinal fluids often cause insufficient bioavailability. The enhancement in the purity of Ribociclib or its succinate salt and crystalline arrangement of novel polymorphic forms (as disclosed in the present invention) which is free of process related impurities inherently, increases the solubility of Ribociclib or its succinate salt, which plays a major role for enhancement of drug dissolution rate in solid oral dosage forms.

Drying may be also be performed by any conventional process not limited to spray drying or distillation to remove the solvent. Drying may be performed under reduced pressure conditions also. Reduced pressure conditions may be suitably utilized by person skilled in the art in order to obtain the dried material. The drying may be performed at a temperature ranging from 50-85° C. for a time ranging from 5 to 10 hours depending upon the physical attributes of the end product obtained i.e. Pure Ribociclib or its succinate salt, which is obtained according to the present invention is having purity greater than 99.5%.

In another embodiment of the present invention the substantially pure Ribociclib or its succinate salt obtained by the processes of the present application may be taken as such in crystalline form for manufacture of solid dosage forms like tablets, capsules and/or for manufacture of oral liquids.

In another embodiment of the present invention the substantially pure crystalline or amorphous form of Ribociclib or its succinate salt obtained by the processes of the present application may be manufactured as the amorphous form by processing with polymers like hydroxypropyl methylcellulose acetate succinate (HPMC-AS).

In another embodiment, the substantially pure crystalline or amorphous form of Ribociclib or its succinate salt obtained by the processes of the present application may be formulated as solid compositions for oral administration in the form of capsules, tablets, pills, powders or granules. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerin, propylene glycol or liquid paraffin.

In one embodiment of the present invention, it also includes premix comprising one or more pharmaceutically acceptable excipients in the range of 1 to 50% w/w with the substantially pure crystalline or amorphous form of Ribociclib or its succinate salt, while retaining the crystalline nature of the premix.

The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising substantially pure crystalline or amorphous form of Ribociclib or its succinate salt obtained as per the present application process—include, but are not limited to diluents such as starch, pregelatinized starch, lactose, powdered cellulose, microcrystalline cellulose, di-calcium phosphate, tri-calcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions derived from substantially pure crystalline or amorphous form of Ribociclib or its succinate salt of the present application may also comprise to include the pharmaceutically acceptable carrier used for the preparation of solid dispersion, wherever utilized in the desired dosage form preparation.

The following examples illustrate the nature of the invention and are provided for illustrative purposes only and should not be construed to limit the scope of the invention.

EXAMPLES

Example-1

Preparation of Ribociclib Mono Succinate Form SRS-I

Succinic acid (0.285 g, 0.0024 mol) was charged into a reaction flask containing water (5.0 mL) at 25-30° C. Reaction mass was heated to 50-55° C. Charged Ribociclib base (1.0 g, 0.0023 mol) at 50-55° C. and stirred for 2 hours minutes at 50-55° C. Reaction mass filtered through 0.22 micron filter and washed with water (2.0 mL). Concentrated the reaction mass under vacuum at 65-70° C. with Heptane, isolated the product. Dried the material under vacuum at 55-60° C. for 12-15 hours.

Yield: 1.2 g.

Example-2

Preparation of Ribociclib Mono Succinate Form SRS-I

Succinic acid (0.142 g, 0.0012 mol) was charged into a reaction flask containing water (2.5 mL) at 25-30° C. Reaction mass was heated to 50-55° C. Charged Ribociclib base (0.5 g, 0.00115 mol) at 50-55° C. and stirred for 2 hours minutes at 50-55° C. Reaction mass filtered through 0.22 micron filter and washed with water (1.0 mL). Concentrated the reaction mass under vacuum at 65-70° C., Added 1-Propanol (5.0 mL) and again concentrated the reaction mass under vacuum at 65-70° C., isolated the product. Dried the material at 55-60° C. under vacuum for 12-15 hours.

Yield: 0.53 g.

Example-3

Preparation of Ribociclib Mono Succinate Form SRS-I

Succinic acid (0.142 g, 0.0012 mol) was charged into a reaction flask containing water (2.5 mL) at 25-30° C. Reaction mass was heated to 50-55° C. Charged Ribociclib base (0.5 g, 0.00115 mol) at 50-55° C. and stirred for 30 minutes at 50-55° C. Reaction mass filtered through 0.22 micron filter and washed with water (1.0 mL). Concentrated the reaction mass under vacuum at 65-70° C., added t-Butanol (5.0 mL) and concentrated the reaction mass under vacuum at 65-70° C., isolated the product. Dried the material at 55-60° C. under vacuum for 12-15 hours.

Yield: 0.50 g

Example-4

Preparation of Ribociclib Mono Succinate Form SRS-I

Succinic acid (0.142 g, 0.0012 mol) was charged into a reaction flask containing water (2.5 mL) at 25-30° C. Reaction mass was heated to 50-55° C. Charged Ribociclib base (0.5 g, 0.00115 mol) at 50-55° C. and stirred for 30 minutes at 50-55° C. Reaction mass filtered through 0.22 micron filter and washed with water (1.0 mL). Concentrated the reaction mass under vacuum at 65-70° C., added Acetone (5.0 mL) and concentrated the reaction mass under vacuum at 65-70° C., isolated the product. Dried the material at 55-60° C. under vacuum for 12-15 hours.

Yield: 0.50 g

Example-5

Preparation of Ribociclib DMSO Solvate

Ribociclib base (0.5 g, 0.00115 mol) charged into a reaction flask containing DMSO (4.0 mL) at 25-30° C. Reaction mass temperature heated to 55-60° C. Stirred the reaction mass for 1.0 hour at 55-60° C. Reaction mass cooled to 25-30° C. and stirred for 1.0 hour at 25-30° C. Filtered and washed with DMSO (1.0 mL). Dried the material at 55-60° C. under vacuum for 12-15 hours.

Yield: 0.27 g.

Example-6

Process for the Preparation of Crystalline Ribociclib Base

Ribociclib base (0.5 g, 0.00115 mol) was charged into a reaction flask containing methanol (100 ml) at 25-30° C. Reaction mass was stirred for 5 minutes and filtered directly into a buchi rotavapor flask. Rotavaporization was performed at 60° C. with step-wise decrease of pressure from 916 mbar to 50 mbar for 120 minutes to yield crystalline Ribociclib base having PXRD pattern as disclosed in FIG. 9.

Yield: 0.4 g

Example-7

Preparation of Ribociclib 2-Methoxy Ethanol Solvate

Ribociclib base (0.5 g, 0.00115 mol) charged into a reaction flask containing 2-Methoxy ethanol (4.0 mL) at 25-30° C. Reaction mass temperature heated to 55-60° C. Stirred the reaction mass for 1.0 hour at 55-60° C. Reaction mass cooled to 25-30° C. and stirred for 1.0 hour at 25-30° C. Filtered and washed with 2-Methoxy ethanol (1.0 mL). Dried the material at 55-60° C. under vacuum for 12-15 hours.

Yield: 0.13 g.

Example-8

Process for the Preparation of Amorphous Ribociclib Mono Succinate

Ribociclib mono succinate (500 mg) obtained from any of the prior art process was charged into a reaction flask containing methanol (50 ml) at 25-30° C. The reaction mass was stirred for 5 minutes and filtered directly into a buchi rotavapor flask. Rotavaporization was performed at 60° C. with step-wise decrease of pressure from 916 mbar to 50 mbar for 120 minutes to yield amorphous Ribociclib mono succinate having PXRD pattern as disclosed in FIG. 8.

Yield: 350 mg

While the foregoing pages provide a detailed description of the preferred embodiments of the invention, it is to be understood that the summary, description and examples are for illustrative purpose only of the core of the invention and non-limiting in their scope. Furthermore, as many changes may be made to the invention without departing from the scope of the invention, it is intended that all material contained herein be interpreted as illustrative of the invention and not in a limiting sense.

We claim:

1. Crystalline Ribociclib mono succinate Form-SRS-I characterized by X-ray powder diffraction pattern comprising characteristic 2θ° peaks at 9.0, 13.0, 15.2, 16.5, 17.3, 18.3, 20.0, 21.4, 21.6, 22.1, 23.6, 23.9 and 28.0±0.2 2θ°.

2. Crystalline Ribociclib mono succinate Form-SRS-I according to claim 1, further characterized by X-ray powder diffraction pattern comprising at 2θ° peaks selected from 4.8, 10.7, 13.5, 14.2, 16.2, 18.0, 19.2, 20.9, 22.7, 23.1, 24.4, 25.4, 26.2, 26.7 and 28.4±0.2 2θ°.

3. Crystalline Ribociclib mono succinate Form-SRS-I according to claim 1, further characterized by DSC isotherm comprising endothermic peaks ranging between 175 to 185° C.

4. Crystalline Ribociclib mono succinate Form-SRS-I characterized by X-ray powder diffraction pattern comprising characteristic 2θ° peaks at 9.0, 13.0, 15.2, 16.5, 17.3, 18.3, 20.0, 21.4, 21.6, 22.1, 23.6, 23.9 and 28.0±0.2 2θ°, wherein the process for the preparation of Crystalline Ribociclib mono succinate Form-SRS-I comprises the steps of:
   a) dissolving succinic acid in first solvent;
   b) adding Ribociclib;
   c) concentrating the reaction mass;
   d) optionally adding second solvent followed by distillation; and
   e) isolate the crystalline Ribociclib mono succinate.

5. Crystalline Ribociclib mono succinate Form-SRS-I according to claim 4, wherein solvent used in step (a) is selected from C1-5-alcohols or Methoxy ethanol, ethoxy methanol or C3-6 Ketones or C1-8 alkanes or dimethyl formamide or dimethyl acetamide or N-methyl pyrrolidine or halogenated organic solvents or Ethers or sulphoxides or esters or water or mixtures thereof.

6. Crystalline Ribociclib mono succinate Form-SRS-I according to claim 4, wherein solvent used in step (d) is selected from C1-5-alcohols or Methoxy ethanol, ethoxy methanol or C3-6 Ketones or C1-8 alkanes or dimethyl formamide or dimethyl acetamide or N-methyl pyrrolidine or halogenated organic solvents or Ethers or sulphoxides or esters or water or mixtures thereof.

* * * * *